US009843074B2

(12) United States Patent
Röschenthaler et al.

(10) Patent No.: US 9,843,074 B2
(45) Date of Patent: Dec. 12, 2017

(54) ELECTROLYTE SALT FOR LITHIUM-BASED ENERGY STORES

(71) Applicants: WESTFÄLISCHE WILHELMS-UNIVERSITÄT MÜNSTER, Munster (DE); JACOBS UNIVERSITY BREMEN GGMBH, Bremen (DE)

(72) Inventors: Gerd-Volker Röschenthaler, Bremen (DE); Martin Winter, Munster (DE); Stefano Passerini, Munster (DE); Katja Vlasov, Mannheim (DE); Nataliya Kalinovich, Bremen (DE); Christian Schreiner Schreiner, Biberbach (DE); Raphael Wilhelm Schmitz, Munster (DE); Ansgar Romek Müller, Bad Bentheim (DE); Rene Schmitz, Mannheim (DE); Tanja Schedlbauer, Munster (DE); Alexandra Lex-Balducci, Munster (DE); Miriam Kunze, St. Andreasberg (DE)

(73) Assignee: WESTFÄLISCHE WILHELMS-UNIVERSITÄT MÜNSTER, Münster (DE)

( * ) Notice: Subject to any disclaimer, the term of this patent is extended or adjusted under 35 U.S.C. 154(b) by 463 days.

(21) Appl. No.: 14/379,524

(22) PCT Filed: Feb. 27, 2013

(86) PCT No.: PCT/EP2013/053949
§ 371 (c)(1),
(2) Date: Aug. 19, 2014

(87) PCT Pub. No.: WO2013/127866
PCT Pub. Date: Sep. 6, 2013

(65) Prior Publication Data
US 2015/0044573 A1 Feb. 12, 2015

(30) Foreign Application Priority Data

Feb. 29, 2012 (DE) .................. 10 2012 101 670

(51) Int. Cl.
*H01M 10/0567* (2010.01)
*C01D 15/00* (2006.01)
*C07C 309/10* (2006.01)
*H01G 11/62* (2013.01)
*H01M 10/052* (2010.01)
*H01M 10/0525* (2010.01)
*H01M 10/0568* (2010.01)
*H01M 10/0569* (2010.01)
*C07C 309/65* (2006.01)
*H01M 10/0565* (2010.01)
*H01G 11/06* (2013.01)
*H01G 11/60* (2013.01)

(52) U.S. Cl.
CPC ........ *H01M 10/0567* (2013.01); *C01D 15/00* (2013.01); *C07C 309/10* (2013.01); *C07C 309/65* (2013.01); *H01G 11/62* (2013.01); *H01M 10/052* (2013.01); *H01M 10/0525* (2013.01); *H01M 10/0565* (2013.01); *H01M 10/0568* (2013.01); *H01M 10/0569* (2013.01); *H01G 11/06* (2013.01); *H01G 11/60* (2013.01); *H01M 2300/0025* (2013.01); *H01M 2300/0028* (2013.01); *H01M 2300/0034* (2013.01); *H01M 2300/0037* (2013.01); *Y02E 60/13* (2013.01)

(58) Field of Classification Search
CPC ..... H01M 10/0567; H01M 2300/0034; H01M 10/0525; H01M 10/0565; H01M 10/0569; H01M 10/052; H01M 10/0568; C07C 309/65; C07C 309/10; C01D 15/00; H01G 11/62
See application file for complete search history.

(56) References Cited

U.S. PATENT DOCUMENTS

| 5,241,110 | A | * | 8/1993 | Navarrini | ............. | B01J 31/0224 562/111 |
| 5,374,770 | A | * | 12/1994 | Navarrini | ............. | B01J 31/0224 562/111 |
| 5,916,708 | A | * | 6/1999 | Besenhard | ............ | H01M 6/164 429/199 |
| 6,506,516 | B1 | | 1/2003 | Wietelmann et al. | | |
| 6,855,476 | B2 | | 2/2005 | Ferreira et al. | | |
| 2006/0276670 | A1 | | 12/2006 | Junk et al. | | |
| 2007/0066822 | A1 | | 3/2007 | Harmer et al. | | |

FOREIGN PATENT DOCUMENTS

| DE | 000019829030 | | 10/1999 |
| EP | 0466483 | | 1/1992 |
| JP | 2000077099 | * | 3/2000 |

OTHER PUBLICATIONS

JP 2000077099 MT.*
Temple et al "The Reaction of Sulfuryl Fluoride and Sulfonyl Fluorides with Fluoro Olefins" The Journal of Organic Chemistry (JOC.*
Hu et al Chem. Rev. 2004, 104, 4303-4417.*
R. Arvai et al: "New aryl-containing fluorinated sulfonic acids and their ammonium salts, useful as electrolytes for fuel cells or ionic liquids", Journal of Fluorine Chemistry, Bd. 129, Nr. 10, Oct. 1, 2008 (Oct. 1, 2008), Seiten 1029-1035, XP025468252, ISSN: 0022-1139, DOI: 10.1016/J.JFLUCHEM.2008.06.009 [gefunden am Jun. 20, 2008].
An English translation of International Search Report issued in connection with International Application No. PCT/EP2013/053949 dated Apr. 24, 2013.
An English Translation of International Prelimnary Report on Patentability Chapter I issued in connection with International Application No. PCT/EP2013/053949 dated Sep. 2, 2014.

* cited by examiner

*Primary Examiner* — Alex Usyatinsky
(74) *Attorney, Agent, or Firm* — Davidson, Davidson & Kappel, LLC

(57) ABSTRACT

The invention relates to lithium 1-trifluoromethoxy-1,2,2,2-tetra-fluoroethanesulphonate, the use of lithium 1-trifluoromethoxy-1,2,2,2-tetra-fluoroethanesulphonate as electrolyte salt in lithium-based energy stores and also ionic liquids comprising 1-trifluoro-methoxy-1,2,2,2-tetrafluoro-ethane-sulphonate as anion.

7 Claims, 6 Drawing Sheets

ELECTROLYTE SALT FOR LITHIUM-BASED ENERGY STORES

This application is a U.S. national phase application under 35 U.S.C. of §371 of International Application No. PCT/EP2013/053949, filed on Feb. 27, 2013, which claims priority to DE 10 2012 101 670.4, filed on Feb. 29, 2012, the disclosures of which are all hereby incorporated by reference herein.

FIELD OF THE INVENTION

The invention relates to a conductive salt and to an electrolyte for lithium-based energy storage means.

BACKGROUND OF THE INVENTION

Lithium-ion technology is the leading technology in the field of rechargeable battery storage systems for portable electronics. Because of their high cell voltage, their superior energy density and power density and their exceedingly low self-discharge, lithium-ion batteries have high potential for these applications. Currently, lithium hexafluorophosphate ($LiPF_6$) is being used as conductive salt in commercially available lithium-ion batteries. Lithium hexafluorophosphate has a relatively high conductivity, but has considerable disadvantages because of low thermal stability and the toxicity of its combustion products.

There are therefore intensive efforts to develop alternative lithium salts which can replace $LiPF_6$ as conductive salt. The lithium salts that have been developed in the last few years are frequently complex boron- or phosphorus-containing anions having nonaromatic chelating agents such as oxalate, for example lithium bis(oxalato)borate (LiBOB), which is disclosed in DE 198 29 030 C1. It is disadvantageous, however, that bis(oxalato)borate has only a low solubility in the carbonates that are typically used as solvents in electrolytes. Moreover, LiBOB-based electrolytes have a lower conductivity compared to $LiPF_6$, especially at low temperatures, and a higher viscosity.

In spite of a multitude of salts and solvents, no suitable substitute has been found as yet for $LiPF_6$ as conductive salt in carbonate mixtures. There is therefore a need for alternative lithium salts for use in lithium-ion batteries.

SUMMARY OF THE INVENTION

It is therefore an object of the present invention to provide a compound which overcomes at least one of the aforementioned disadvantages of the prior art. More particularly, it was an object of the present invention to provide a lithium compound suitable as a conductive salt.

This object is achieved by the compound lithium 1-trifluoromethoxy-1,2,2,2-tetrafluoroethanesulfonate. Lithium 1-trifluoromethoxy-1,2,2,2-tetrafluoroethane-sulfonate is also referred to as lithium 1,2,2,2-tetrafluoro-1-(trifluoromethoxy)ethanesulfonate.

It has been found that, surprisingly, lithium 1-trifluoromethoxy-1,2,2,2-tetrafluoroethanesulfonate has a good lithium-ion conductivity and a high electrochemical stability. Advantageously, lithium 1-trifluoromethoxy-1,2,2,2-tetrafluoroethanesulfonate is usable as conductive salt within a wide temperature range. Moreover, cells in which electrolytes comprising lithium 1-trifluoromethoxy-1,2,2,2-tetrafluoroethane-sulfonate as conductive salt were used show good cycling stability and retention of capacity.

In addition, a great advantage of lithium 1-trifluoromethoxy-1,2,2,2-tetrafluoroethanesulfonate is a good thermal stability. It is especially advantageous that lithium 1-trifluoromethoxy-1,2,2,2-tetrafluoroethane-sulfonate, even at high temperatures, shows almost no sign of breakdown, if any. Thus, in thermal aging experiments, it was found that, over the course of prolonged storage of an electrolyte comprising lithium 1-trifluoromethoxy-1,2,2,2-tetrafluoroethane-sulfonate in carbonate solvents at 95° C., no carbonate breakdown products that occur in the course of thermal storage of $LiPF_6$ in carbonate mixtures are detectable in the electrolyte.

In this way, compared to the use of $LiPF_6$ as conductive salt, it is possible to provide a considerable improvement in operational reliability. In an especially advantageous manner, this enables use in the high-temperature range. Lithium 1-trifluoromethoxy-1,2,2,2-tetrafluoroethanesulfonate especially exhibits lower toxicity of the combustion products than $LiPF_6$. Lithium 1-trifluoromethoxy-1,2,2,2-tetrafluoroethane-sulfonate is therefore advantageously suitable as conductive salt for commercial lithium-ion batteries. Moreover, the anodic stability of an electrolyte comprising lithium 1-trifluoromethoxy-1,2,2,2-tetrafluoroethanesulfonate in carbonate mixtures on polished platinum, at more than 5 V, was advantageously also found to be sufficient for cycling with the standard cathode materials.

The present invention further relates to the use of lithium 1-trifluoromethoxy-1,2,2,2-tetrafluoroethane-sulfonate in lithium-based energy storage means, especially as conductive salt. More particularly, lithium 1-trifluoromethoxy-1,2,2,2-tetrafluoroethane-sulfonate is usable as conductive salt in electrolytes for lithium-based energy storage means. Primary and secondary lithium-based energy storage means are preferably selected from the group comprising lithium batteries, lithium-ion batteries, lithium-ion accumulators, lithium polymer batteries and/or lithium-ion capacitors. More particularly, lithium 1-trifluoro-methoxy-1,2,2,2-tetrafluoroethanesulfonate is suitable as a conductive salt for a lithium-ion battery or a lithium-ion accumulator.

It is advantageously possible, through use of lithium 1-trifluoromethoxy-1,2,2,2-tetrafluoroethanesulfonate in lithium-based energy storage means, to provide a thermally stable conductive salt. In this way, a lithium-based energy storage means is usable within a wide temperature range. Preferably, lithium 1-trifluoromethoxy-1,2,2,2-tetrafluoroethanesulfonate is usable in electrolytes for lithium-based energy storage means in a concentration in the range from ≥0.1 M to ≤2 M, preferably in the range from ≥0.5 M to ≤1.5 M, more preferably in the range from ≥0.7 M to ≤1.2 M. More particularly, lithium 1-trifluoromethoxy-1,2,2,2-tetrafluoroethanesulfonate is usable in a concentration of 1 M.

The charge transport in lithium-based electrochemical energy storage means is effected by means of an electrolyte. The conductive salt of a liquid electrolyte is therefore preferably present dissolved in a solvent. The electrolyte comprises lithium 1-trifluoro-methoxy-1,2,2,2-tetrafluoroethanesulfonate, preferably dissolved in an organic solvent. The electrolyte is producible, for example, by introducing and dissolving lithium 1-trifluoromethoxy-1,2,2,2-tetrafluoroethane-sulfonate into a solvent or a solvent mixture.

The invention further relates to an electrolyte for a lithium-based energy storage means comprising lithium 1-trifluoromethoxy-1,2,2,2-tetrafluoroethanesulfonate. Electrolytes for lithium-based energy storage means comprising lithium 1-trifluoromethoxy-1,2,2,2-tetrafluoroethanesulfonate as conductive salt have the particular advantage of a good thermal and electrochemical stability.

The electrolyte preferably comprises an organic solvent, an ionic liquid and/or a polymer matrix. The electrolyte preferably comprises an organic solvent and lithium 1-trifluoromethoxy-1,2,2,2-tetrafluoroethane-sulfonate. It has been found that lithium 1-trifluoromethoxy-1,2,2,2-tetrafluoroethanesulfonate has a good solubility in organic solvents, especially mixtures comprising cyclic or linear carbonates. This advantageously enables the use of lithium 1-trifluoromethoxy-1,2,2,2-tetrafluoroethanesulfonate in the liquid electrolytes used in commercial lithium-ion batteries.

In preferred embodiments, the organic solvent is selected from the group comprising ethylene carbonate, propylene carbonate, diethyl carbonate, dimethyl carbonate, ethyl methyl carbonate, acetonitrile, glutaronitrile, adiponitrile, pimelonitrile, gamma-butyrolactone, gamma-valerolactone, dimethoxyethane, 1,3-dioxolane, methyl acetate and/or a mixture thereof. Suitable organic solvents are selected from the group comprising cyclic carbonates such as ethylene carbonate and propylene carbonate and/or linear carbonates such as diethyl carbonate, dimethyl carbonate and ethyl methyl carbonate. Further suitable organic solvents are selected from the group comprising gamma-butyrolactone and/or gamma-valerolactone. The organic solvent is preferably selected from the group comprising ethylene carbonate, diethyl carbonate, dimethyl carbonate, ethyl methyl carbonate, gamma-butyrolactone, gamma valerolactone and/or mixtures thereof.

A preferred solvent is ethylene carbonate. According to the IUPAC nomenclature, ethylene carbonate is also referred to as 1,3-dioxolan-2-one. Ethylene carbonate is commercially available and has a high boiling point and a high flashpoint. It is also advantageous that ethylene carbonate enables a high conductivity through good salt dissociation.

In a preferred embodiment, the organic solvent comprises a mixture of ethylene carbonate and at least one further organic solvent, preferably selected from the group comprising gamma-butyrolactone and/or diethyl carbonate. The organic solvent preferably comprises a mixture of ethylene carbonate and gamma-butyrolactone. In solvent mixtures comprising ethylene carbonate and gamma-butyrolactone, it was advantageously possible to achieve a high conductivity within a temperature range from −20° C. to +60° C. More particularly, in solvent mixtures comprising gamma-butyrolactone, it is possible to achieve high conductivities within a temperature range from −30° C. to +60° C. Suitable examples are, for example, binary mixtures of carbonates, especially of ethylene carbonate, with a further carbonate, for example diethyl carbonate, dimethyl carbonate and/or ethyl methyl carbonate, especially diethyl carbonate.

Preferably, the ratio of ethylene carbonate and the at least one further organic solvent, preferably gamma-butyrolactone or diethyl carbonate, is in the range from ≥1:99 to ≤99:1, preferably in the range from ≥1:9 to ≤9:1, preferably in the range from ≥3:7 to ≤1:1. Unless stated otherwise, the ratio reported is based on the proportions by weight of the solvents.

Preference is also given to ternary mixtures comprising at least one carbonate as solvent. Especially preferred mixtures are those of ethylene carbonate with a further solvent, for example gamma-butyrolactone or diethyl carbonate, and a compound suitable for forming a solid electrolyte interphase (SEI). The electrolyte may therefore further comprise additives, especially film-forming electrolyte additives.

In preferred embodiments, the electrolyte comprises a compound selected from the group comprising chloroethylene carbonate, fluoroethylene carbonate, vinylethylene carbonate, ethylene sulfite, ethylene sulfate, propanesulfonates, sulfites, preferably dimethyl sulfite and propylene sulfite, sulfates, optionally F—, Cl— or Br-substituted butyrolactones, phenylethylene carbonate, vinyl acetate and/or trifluoropropylene carbonate.

Among the carbonate-based compounds, preference is given to chlorine- or fluorine-substituted carbonates, especially fluoroethylene carbonate (FEC). The compounds can improve the battery performance, for example the capacity or cycling lifetime. Fluoroethylene carbonate in particular can lead to an improved long-term stability of a cell.

Preferably, the electrolyte comprises an additive, especially a compound selected from the group comprising chloroethylene carbonate, fluoroethylene carbonate, vinylethylene carbonate, ethylene sulfite, ethylene sulfate, propanesulfonates, sulfites, preferably dimethyl sulfite and propylene sulfite, sulfates, optionally F—, Cl— or Br-substituted butyrolactones, phenylethylene carbonate, vinyl acetate and/or trifluoropropylene carbonate, preferably fluoroethylene carbonate, in the range from ≥0.1% by weight to ≤10% by weight, preferably in the range from ≥1% by weight to ≤5% by weight, more preferably in the range from ≥2% by weight to ≤3% by weight, based on the total weight of the electrolyte.

Preferably, the organic solvent comprises a mixture of ethylene carbonate and at least one further organic solvent, preferably selected from the group comprising gamma-butyrolactone, gamma-valerolactone or diethyl carbonate and fluoroethylene carbonate.

Preferably, the ratio of ethylene carbonate and the at least one further organic solvent, preferably selected from the group comprising gamma-butyrolactone, gamma-valerolactone or diethyl carbonate, and an additive, preferably fluoroethylene carbonate, is in the range from ≥98:1:1 to ≤1:1:98, preferably in the range from ≥80:15:5 to ≤15:80:5, more preferably in the range from ≥4.5:4.5:1 to ≤1:1:0.01. Unless stated otherwise, the ratio reported is based on the proportions by weight.

More preferably, the organic solvent comprises a mixture of ethylene carbonate, gamma-butyrolactone and fluoroethylene carbonate, especially in a ratio of 4.5:4.5:1. In a solvent mixture comprising ethylene carbonate, gamma-butyrolactone and fluoroethylene carbonate in a ratio of 4.5:4.5:1, it has advantageously been possible to achieve a good conductivity within a temperature range from −20° C. to +60° C.

Further promising solvents have been found to be ionic liquids which combine a high thermal and electrochemical stability with a high ionic conductivity. This is especially advantageous for use together with lithium 1-trifluoromethoxy-1,2,2,2-tetrafluoroethanesulfonate. Preferred ionic liquids include a cation selected from the group comprising 1-ethyl-3-methylimidazolium ($EMI^+$), 1,2-dimethyl-3-propyl-imidazolium ($DMPI^+$), 1,2-diethyl-3,5-dimethylimidazolium ($DEDMI^+$), trimethyl-n-hexylammonium ($TMHA^+$), N-alkyl-N-methylpyrrolidinium ($PYR_{1R}^+$), N-alkyl-N-methylpiperidinium ($PIP_{1R}^+$) and/or N-alkyl-N-methylmorpholinium ($MORP_{1R}^+$), and an anion selected from the group comprising bis(trifluoromethanesulfonyl)imide ($TFSI^-$), bis(pentafluoroethanesulfonyl)imide ($BETI^-$), bis(fluoro-sulfonyl)imide ($FSI^-$), 2,2,2-trifluoro-N-(trifluoro-methanesulfonyl)acetamide ($TSAC^-$), tetrafluoroborate ($BF_4^-$), pentafluoroethanetrifluoroborate ($C_2F_5BF_3^-$), hexafluorophosphate ($PF_6^-$) and/or tri(pentafluoroethane)trifluorophosphate (($C_2F_5)_3PF_3^-$). Preferred N-alkyl-N-methylpyrrolidinium ($PYR_{1R}^+$) cations are selected from the group comprising N-butyl-N-methylpyrrolidinium ($PYR_{14}^+$) and/or N-methyl-N-propylpyrrolidinium ($PYR_{13}^+$). Preferred ionic liquids are selected from the group comprising N-butyl-N-methylpyrrolidinium bis(trifluoromethanesulfonyl)imide (PYR$_{14}$TFSI) and/or N-methyl-N-propylpyrrolidinium bis(trifluoromethanesulfonyl)imide (PYR$_{13}$TFSI).

Further suitable electrolyte materials are polymer electrolytes, wherein the polymer electrolyte may take the form of a gel polymer electrolyte or solid polymer electrolyte. Solid polyelectrolytes exhibit good properties with regard to the demands on future generations of accumulator. They enable a solvent-free structure which is easy to produce and may take various forms. Furthermore, the energy density can be enhanced, since the three-layer structure of electrolyte-separator-electrolyte can be dispensed with, so that only a thin polymer film is required between the electrodes. Solid electrolytes are generally chemically and electrochemically stable with respect to electrode materials and, moreover, do not escape from the cell. Gel polymer electrolytes usually comprise an aprotic solvent and a polymer matrix.

Preferred polymers for solid polymer electrolytes and gel polymer electrolytes are selected from the group comprising homo- or copolymers of polyethylene oxide (PEO), polypropylene oxide (PPO), polyvinylidene fluoride (PVdF), polyvinylidene fluoride-hexafluoro-propylene (PVdF-HFP), polyacrylonitrile (PAN), polymethylmethacrylate (PMMA), polyethylmethacrylate (PEMA), polyvinyl acetate (PVAc), polyvinyl chloride (PVC), polyphosphazenes, polysiloxanes, polyvinyl alcohol (PVA) and/or homopolymers and (block) copolymers comprising functional side chains selected from the group comprising ethylene oxide, propylene oxide, acrylonitrile and/or siloxanes.

In preferred embodiments, the concentration of lithium 1-trifluoromethoxy-1,2,2,2-tetrafluoroethanesulfonate in the electrolyte is in the range from ≥0.1 M to ≤2 M, preferably in the range from ≥0.5 M to ≤1.5 M, more preferably in the range from ≥0.7 M to ≤1.2 M. In a particularly preferred embodiment, the concentration of lithium 1-trifluoromethoxy-1,2,2,2-tetrafluoroethanesulfonate in the electrolyte is 1 M. Advantageously, such concentrations of lithium 1-trifluoromethoxy-1,2,2,2-tetrafluoroethanesulfonate lead to a good conductivity.

The invention further relates to a lithium-based energy storage means, preferably a lithium battery, lithium-ion battery, lithium-ion accumulator, lithium polymer battery or lithium-ion capacitor, comprising lithium 2-trifluoromethoxy-1,2,2,2-tetrafluoroethanesulfonate. The invention further relates to a lithium-based energy storage means, preferably a lithium battery, lithium-ion battery, lithium-ion accumulator, lithium polymer battery or lithium-ion capacitor, comprising an electrolyte comprising lithium 1-trifluoromethoxy-1,2,2,2-tetrafluoroethanesulfonate according to the invention.

The lithium-based energy storage means are suitable for all fields of use, especially including larger systems such as automobiles or as stationary energy storage means for renewable energies.

Lithium 1-trifluoromethoxy-1,2,2,2-tetrafluoroethanesulfonate is preparable by customary synthesis methods. Preference is given to a process for preparing lithium 1-trifluoromethoxy-1,2,2,2-tetrafluoroethanesulfonate, comprising the following steps:
a) reacting 1,1,2-trifluoro-2-(trifluoromethoxy)ethene with sulfuryl difluoride to give 1,2,2,2-tetrafluoro-1-(trifluoromethoxy)ethanesulfonyl fluoride, and
b) reacting 1,2,2,2-tetrafluoro-1-(trifluoromethoxy)-ethanesulfonyl fluoride with lithium hydroxide to give lithium 1-trifluoromethoxy-1,2,2,2-tetrafluoroethanesulfonate.

Preferably, the reaction of 1,1,2-trifluoro-2-(trifluoromethoxy)ethene, $CF_3OCF=CF_2$, with sulfuryl difluoride, $SO_2F_2$, is effected in the presence of catalytic amounts of tetramethylammonium fluoride. The reaction is preferably effected while heating, especially at a temperature in the range from 50° C. to 60° C. The subsequent hydrolysis of 1,2,2,2-tetrafluoro-1-(trifluoromethoxy)ethanesulfonyl fluoride with lithium hydroxide is preferably effected with ethanolic lithium hydroxide solution.

As a precursor, 1,2,2,2-tetrafluoro-1-(trifluoro-methoxy)ethanesulfonyl fluoride is obtained in step a). Advantageously, the reaction of 1,1,2-trifluoro-2-(trifluoromethoxy)ethene with sulfuryl difluoride to give 1,2,2,2-tetrafluoro-1-(trifluoromethoxy)ethanesulfonyl fluoride is less complex and easier to manage than a complicated reaction of trifluoromethyl hypofluorite, $CF_3OF$, which is difficult to manage and difficult to obtain, with trifluorovinylsulfonyl fluoride, $CF_2=CFSO_2F$. In addition, the process according to the invention can achieve a greater yield.

Lithium 1-trifluoromethoxy-1,2,2,2-tetrafluoroethanesulfonate is usable as conductive salt in an electrolyte comprising, for example, an ionic liquid in lithium-based energy storage means.

Ionic liquids are usable as nonaqueous electrolytes, particularly for electrochemical uses, for example in batteries or electrochemical capacitors, but also for electroplating, catalysis or chemical reactions. Ionic liquids having a preferably broad electrochemical window and low hygroscopicity are accordingly usable advantageously not just for electrochemical applications.

The invention further relates to an ionic liquid comprising 1-trifluoro-methoxy-1,2,2,2-tetrafluoroethanesulfonate and an organic cation selected from the group comprising alkylammonium, pyridinium, pyrazolium, pyrrolium, pyrrolinium, piperidinium, pyrrolidinium, imidazolium and/or sulfonium compounds. Preferably, the organic cation is selected from the group comprising alkylammonium, pyridinium, pyrazolium, pyrrolium, pyrrolinium, piperidinium, pyrrolidinium and/or imidazolium compounds, especially pyrrolidinium and/or imidazolium compounds. Preferably, the cation is selected from the group comprising N-butyl-N-methylpyrrolidinium (PYR14), N-methyl-N-propyl-pyrrolidinium (PYR13), 1-ethyl-3-methylimidazolium (EMIM), 1-ethyl-2,3-dimethylimidazolium (EDiMIM) and/or 1-butyl-3-methylimidazolium (BMIM).

Ionic liquids comprising 1-trifluoromethoxy-1,2,2,2-tetrafluoroethanesulfonate as anion and an organic cation can be used advantageously for electrochemical applications, for example in combination with a lithium salt in lithium-based energy storage means. Also advantageous are uses in solar cells or fuel cells. Advantageously, ionic liquids comprising fluorinated anions are also usable as hydraulic fluid or inert liquid diluent for highly reactive chemicals.

BRIEF DESCRIPTION OF THE DRAWINGS

Examples and figures which serve to illustrate the present invention are adduced hereinafter.

The figures here show.

Figure 3:
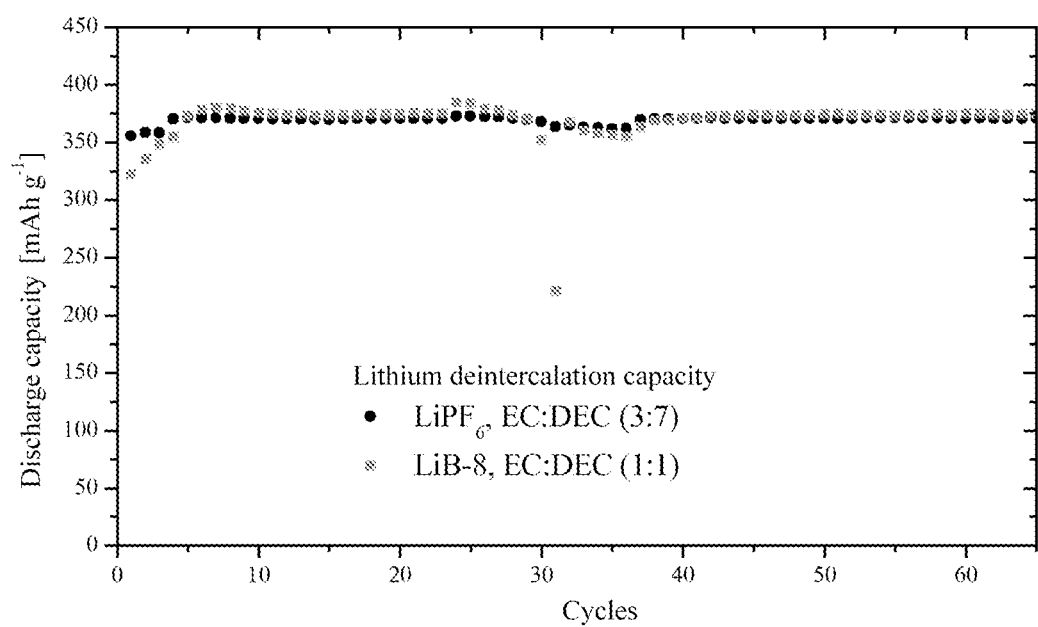

FIG. 3 shows the discharge capacity of a lithium-ion half-cell with 1 M lithium 1-trifluoro-methoxy-1,2,2,2-tetrafluoroethanesulfonate (LiB-8) in a solvent mixture of ethylene carbonate and diethyl carbonate (EC:DEC) in a ratio of 1:1 and graphite as working electrode compared to LiPF$_6$. The discharge capacity is plotted against the cycle number.

Figure 4:
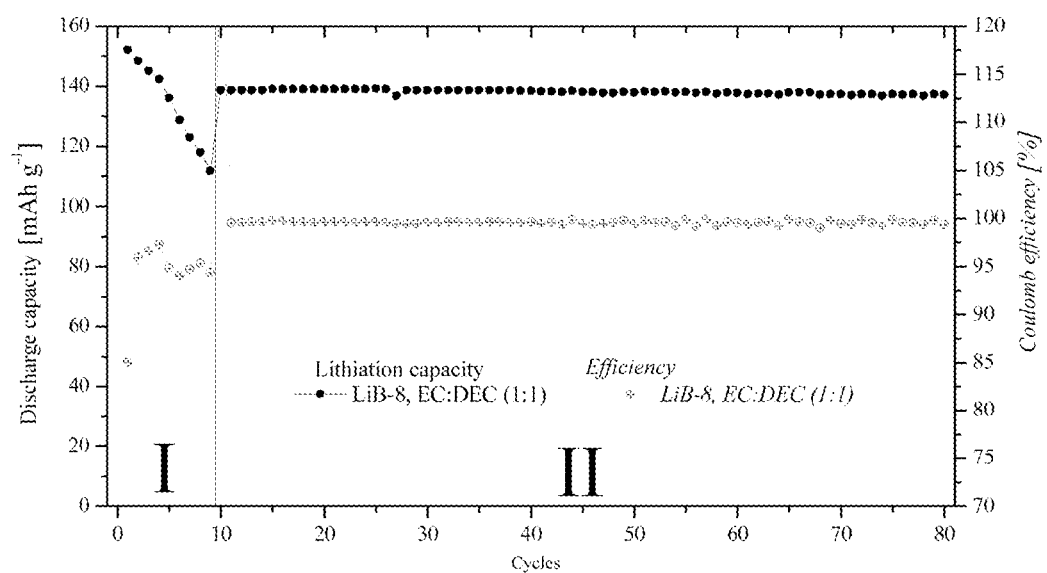

FIG. 4 shows the discharge capacity and efficiency of a lithium-ion half-cell with 1 M lithium 1-trifluoromethoxy-1,2,2,2-tetrafluoroethane-sulfonate (LiB-8) in a solvent mixture of ethylene carbonate and diethyl carbonate (EC:DEC) in a ratio of 1:1. The working electrode used was the cathode material nickel manganese cobalt oxide. The discharge capacity is plotted against the cycle number.

Figure 5:
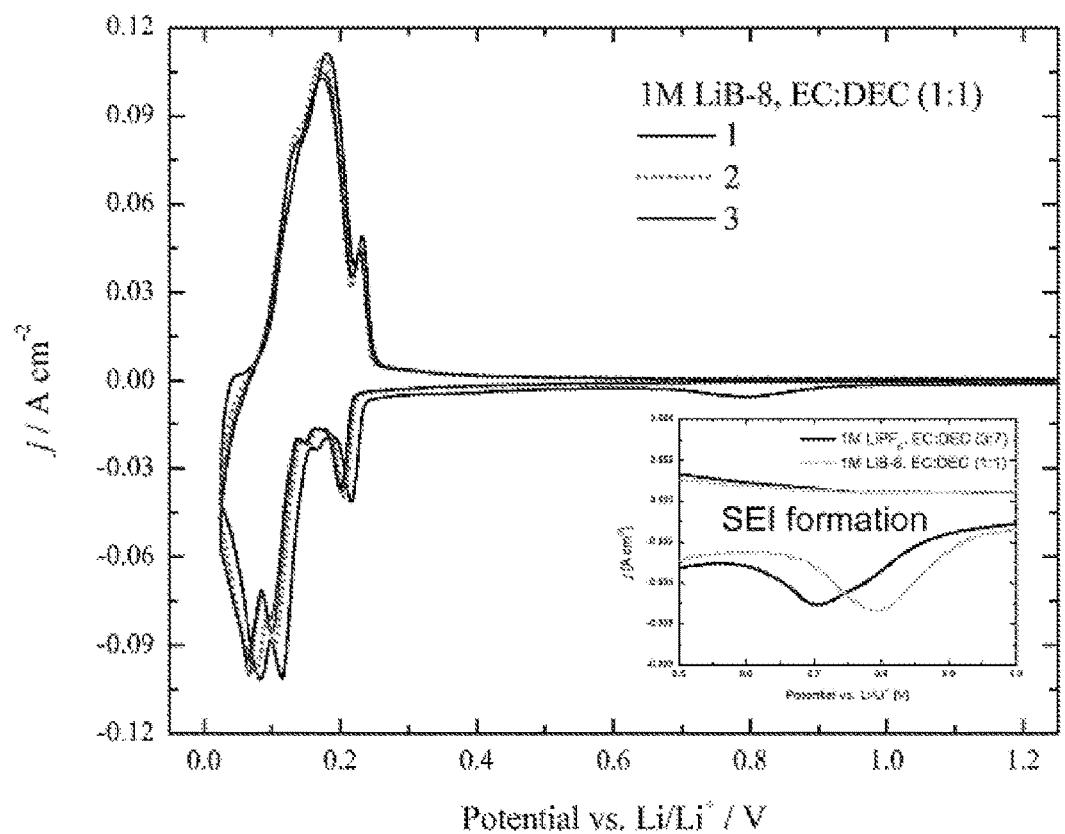

FIG. 5 shows the cyclic voltammetry of a 1 M solution of lithium 1-trifluoromethoxy-1,2,2,2-tetrafluoroethanesulfonate (LiB-8) in a solvent mixture of ethylene carbonate and diethyl carbonate (EC:DEC) in a ratio of 1:1 on a graphite anode for three cycles (1), (2) and (3).

Figure 6:
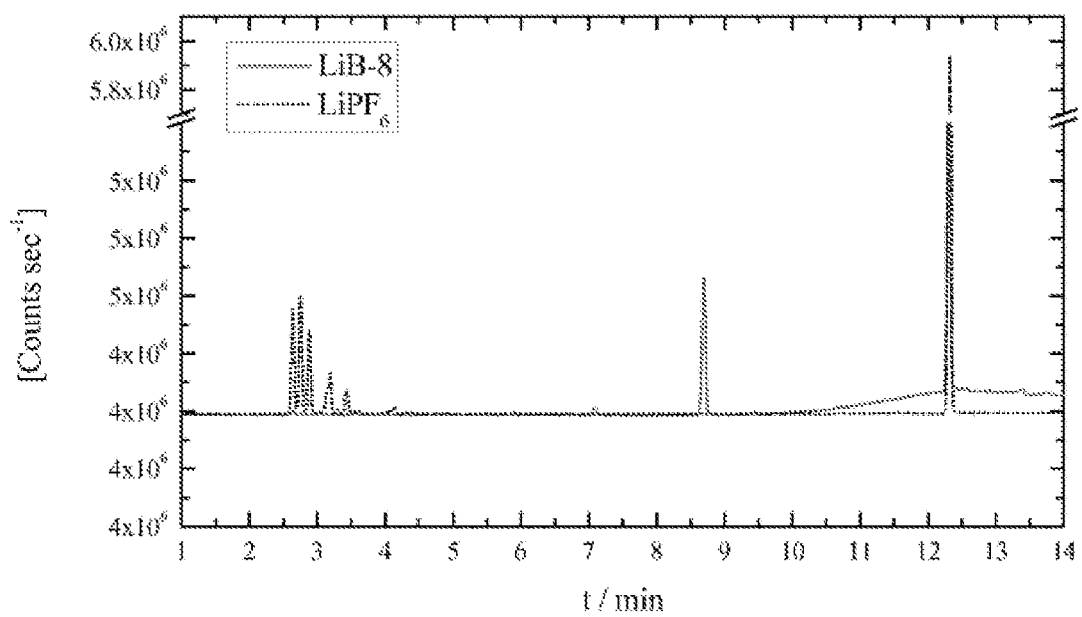

FIG. 6 shows the breakdown products of the thermal aging at 95° C. of a 1 M solution of lithium 1-trifluoromethoxy-1,2,2,2-tetrafluoroethane-sulfonate (LiB-8) in ethylene carbonate and diethyl carbonate (EC:DEC) in a ratio of 1:1 compared to LiPF$_6$ in EC:DEC in a ratio of 3:7.

DETAILED DESCRIPTION OF THE INVENTION

Example 1

Preparation of lithium 1-trifluoromethoxy-1,2,2,2-tetrafluoroethanesulfonate a) Preparation of 1,2,2,2-tetrafluoro-1-(trifluoromethoxy)ethanesulfonyl fluoride 10 mg of tetramethylammonium fluoride (ABCR) were suspended in 10 ml of dry bis(2-methoxyethyl) ether (diglyme, ABCR). At −197° C., 36 mmol of sulfuryl difluoride (ABCR) and 36 mmol of 1,1,2-trifluoro-2-(trifluoromethoxy)ethene (ABCR) were condensed in. The reaction mixture was heated to 60° C. for 12 h and then the product was distilled. 1,2,2,2-Tetrafluoro-1-(trifluoromethoxy)ethanesulfonyl fluoride was obtained as a colorless liquid in a yield of 92%.

b) Preparation of lithium-1,2,2,2-tetrafluoro-1-(trifluoromethoxy)ethanesulfonate 20 mmol of the 1,2,2,2-tetrafluoro-1-(trifluoro-methoxy) ethanesulfonyl fluoride prepared in step a) were dissolved in 10 ml of ethanol (ROTH). At 0° C., 40 mmol of lithium hydroxide (ROTH) were added. The suspension was stirred at room temperature (20±3° C.) for 2 h, then centrifuged for 15 min, and the liquid phase was decanted off. The solvent was drawn off and the product was dried under reduced pressure (0.001 mm) at 60° C. for 6 h. The yield was 65%. Lithium 1-trifluoromethoxy-1,2,2,2-tetrafluoroethanesulfonate was dried before use at 60° C. for 24 hours.

Example 2

Determination of the conductivity of lithium 1-trifluoromethoxy-1,2,2,2-tetrafluoroethanesulfonate The conductivity of lithium 1-trifluoromethoxy-1,2,2,2-tetrafluoroethanesulfonate was determined in different solvents within a temperature range from −40° C. to +60° C. Mixtures of 50% by weight of ethylene carbonate (EC) (Ferro Corporation, battery grade) and 50% by weight of diethyl carbonate (DEC) (Ferro Corporation, battery grade) (EC:DEC, 1:1), of 50% by weight of ethylene carbonate and 50% by weight of gamma-butyrolactone (γ-BL) (Ferro Corporation, battery grade) (EC:γ-BL, 1:1), and 45% by weight of ethylene carbonate, 45% by weight of gamma-butyrolactone and 10% by weight of fluoroethylene carbonate (Solvay GmbH) (EC:γ-BL:FEC, 4.5:4.5:1) were prepared. In these solvent mixtures were dissolved 217 mg per milliliter of the lithium 1-trifluoromethoxy-1,2,2,2-tetrafluoroethanesulfonate prepared according to example 1, so as to give a concentration of 1 M. For comparison, a 1 M solution of LiPF$_6$ (Sigma-Aldrich, battery grade) in a mixture of 30% by weight of ethylene carbonate and 70% by weight of diethyl carbonate (EC:DEC, 3:7) was prepared.

The conductivity of the electrolytes was analyzed using platinum conductivity measurement cells (Amel Glassware, cell constant 1 cm$^{-1}$) with a potentiostat (Solartron 1287A) in conjunction with an impedance measurement unit (Solartron 1260) within a temperature range from −40° C. to +60° C. (climate-controlled cabinet, Binder MK53). For this purpose, the conductivity measurement cells were first heated to 60° C. and then cooled in temperature intervals of 5° C. to −40° C.

Figure 1:
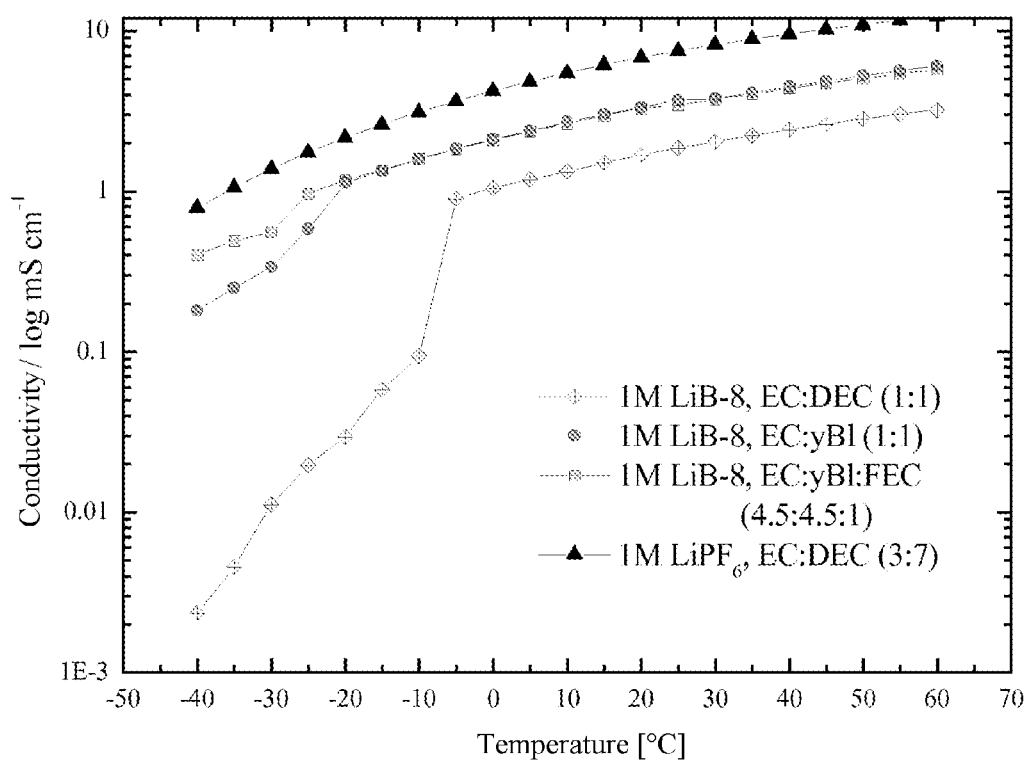
FIG. 1 shows the conductivity of a 1 M solution of lithium 1-trifluoromethoxy-1,2,2,2-tetrafluoroethanesulfonate (LiB-8) in various solvent mixtures as a function of temperature.

FIG. 1 shows the plot of the conductivity of the 1 M solutions of lithium 1-trifluoromethoxy-1,2,2,2-tetrafluoroethanesulfonate (LiB-8) in the various solvent mixtures within the temperature range from −40° C. to +60° C., and that of LiPF$_6$. As can be inferred from FIG. 1, the conductivity in the solvent mixtures of ethylene carbonate and gamma-butyrolactone (EC:γ-BL, 1:1) and of ethylene carbonate, gamma-butyrolactone and fluoroethylene carbonate (EC:γ-BL:FEC) within the temperature range from −40° C. to +0° C. was much higher compared to the conductivity in ethylene carbonate and diethyl carbonate (EC:DEC, 1:1), and attained virtually the conductivity of LiPF$_6$ in an ethylene carbonate and diethyl carbonate (EC:DEC, 3:7) over the entire temperature range.

The conductivity of 1 M lithium 1-trifluoromethoxy-1,2,2,2-tetrafluoroethanesulfonate at 25° C. in the various solvents was 1.8 mS cm$^{-1}$ for a 1:1 mixture of ethylene carbonate and diethyl carbonate (EC:DEC, 1:1), 3.7 mS cm$^{-1}$ for a 1:1 mixture of ethylene carbonate and gamma-butyrolactone (EC:γ-BL, 1:1), and 3.5 mS cm$^{-1}$ for a mixture of ethylene carbonate, gamma butyrolactone and fluoroethylene carbonate (EC:γ-BL:FEC) in a ratio of 4.5:4.5:1.

This shows that lithium 1-trifluoromethoxy-1,2,2,2-tetrafluoroethanesulfonate has a sufficient conductivity at 25° C. in the customary carbonate solvents.

Example 3

Determination of the electrochemical stability of lithium 1-trifluoromethoxy-1,2,2,2-tetrafluoroethane-sulfonate The electrochemical stability of a 1 M solution of lithium 1-trifluoromethoxy-1,2,2,2-tetrafluoroethane-sulfonate prepared according to example 1 in a solvent mixture of 50% by weight of ethylene carbonate and 50% by weight of diethyl carbonate (EC:DEC, 1:1) compared to the stability of a 1 M solution of LiPF$_6$ (Sigma-Aldrich, battery grade) in a mixture of 30% by weight of ethylene carbonate and 70% by weight of diethyl carbonate (EC:DEC, 3:7) was determined by means of linear sweep voltammetry (LSV). In this method, there is a continuous change in the electrode voltage (linear sweep).

The cathodic stability limit, the potential at which reduction sets in, was defined as that potential at which the current density falls below −0.1 mA cm$^{-2}$. The anodic stability limit, the potential at which oxidation sets in, was defined as that potential at which the current density goes above +0.1 mA cm$^{-2}$. The anodic stability in particular depends crucially on the stability of the electrolyte used.

The experiments were conducted in a 3-electrode arrangement in modified Swagelok® T-pieces (tube connector, stainless steel body) with a platinum electrode (eDAQ, model: ET075, diameter 1 mm) as working electrode and lithium foil (diameter 12 mm and 7 mm, respectively, Chemetall) as counterelectrode and reference electrode. In addition, the cell body was lined with a polyester film siliconized on one side (Mylar®, PPI-SP 914, 100 μm) and the electrodes were introduced into the cell body. The electrodes were separated by a nonwoven fabric (Freudenberg®, FS2226E, 6 plies) which had been impregnated with the corresponding electrolyte. The scan rate was 1 mV s$^{-1}$.

Figure 2:
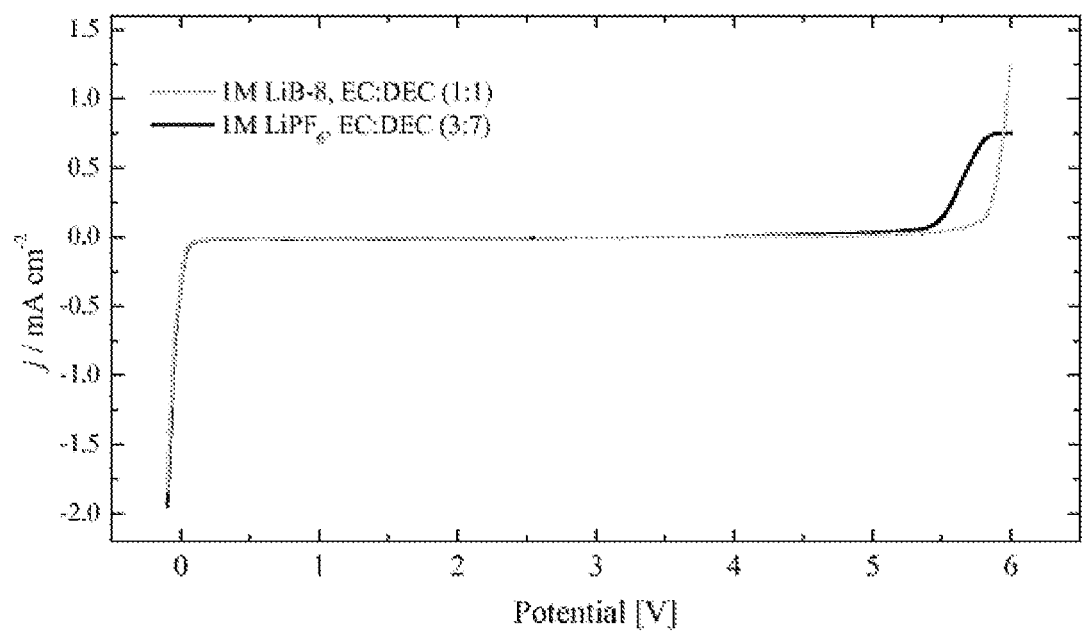
FIG. 2 shows the electrochemical stability window of a 1 M solution of lithium 1-trifluoromethoxy-1,2,2,2-tetrafluoroethanesulfonate (LiB-8) in a solvent mixture of ethylene carbonate and diethyl carbonate (EC:DEC) in a ratio of 1:1 and of LiPF$_6$ in EC:DEC in a ratio of 3:7. The current density is plotted against the potential.

As shown in FIG. 2, in the case of the 1 M lithium 1-trifluoromethoxy-1,2,2,2-tetrafluoroethanesulfonate (LiB-8) electrolyte in a 1:1 mixture of ethylene carbonate and diethyl carbonate, the cathodic stability limit was attained at 0.03 V. The anodic stability of lithium 1-trifluoromethoxy-1,2,2,2-tetrafluoroethane-sulfonate was 5.7 V and is entirely sufficient for use of the electrolyte in combination with high-voltage cathode materials.

This result shows that lithium 1-trifluoromethoxy-1,2,2,2-tetrafluoroethanesulfonate has a sufficiently good electrochemical stability for all electrochemical applications in the customary carbonate solvents.

Example 4

Determination of the cycling performance of lithium 1-trifluoromethoxy-1,2,2,2-tetrafluoroethanesulfonate with a graphite electrode The cycling performance of a 1 M solution of lithium 1-trifluoromethoxy-1,2,2,2-tetrafluoroethanesulfonate prepared according to example 1 was determined in a mixture of 50% by weight of ethylene carbonate and 50% by weight of diethyl carbonate (EC:DEC, 1:1) compared to the cycling of a 1 M solution of LiPF$_6$ in a mixture of 30% by weight of ethylene carbonate and 70% by weight of diethyl carbonate (EC:DEC, 3:7).

The experiments were conducted in a 3-electrode arrangement in modified Swagelok® T-pieces (tube connector, stainless steel body) with a graphite electrode (Timcal T44 graphite material) as working electrode and lithium foil (diameter 12 mm and 5 mm, respectively, Chemetall) as counterelectrode and reference electrode. In addition, the cell body was lined with a polyester film siliconized on one side (Mylar®, PPI-SP 914, 100 μm) and the electrodes were introduced into the cell body. The electrodes were separated by a nonwoven fabric (Freudenberg®, FS2226E, 6 plies) which had been impregnated with the corresponding electrolyte.

The test of the cycling performance comprised several phases. In the first phase, the forming of the graphite (SEI formation) was ensured by three cycles with a constant current C rate of C/5. Thereafter, in the second phase, the cycling performance was tested over 20 cycles at a charge and discharge rate of 1 C. The cell system was kept here at a voltage of 0.025 V for one hour after charging. In the third phase, the graphite was always charged at C/2 and, thereafter, kept at 0.025 V for one hour before the graphite was discharged at different rates. The D rates (discharge rates) used were D/5, D/3, D/2, 1D, 2D, 3D, 5D and 10D. The D rate test was followed by five cycles with charge and discharge rates of C/5, in order to check whether the graphite had been damaged by the stress test. The last phase involved the same cycling parameters as phase 2, but was conducted for 30 cycles.

FIG. 3 shows the discharge capacity or lithium deintercalation capacity of the 1 M solutions of lithium 1-trifluoromethoxy-1,2,2,2-tetrafluoroethane-sulfonate and LiPF$_6$ against the number of cycles of the lithium-ion battery half-cell charged at a C rate of 1 C. As shown in FIG. 3, the half-cell with 1 M lithium 1-trifluoromethoxy-1,2,2,2-tetrafluoroethane-sulfonate had a starting capacity of about 373 mAh g$^{-1}$ after the forming of the cell, which rose with the number of cycles to about 374 mAh g$^{-1}$ in the 15th cycle. This shows the excellent cycling stability of the cell, which corresponds to that of LiPF$_6$.

Example 5

Determination of the cycling performance of lithium 1-trifluoromethoxy-1,2,2,2-tetrafluoroethanesulfonate with NCM cathode The cycling performance on NCM cathodes in a half-cell was conducted as described in example 4 in a 3-electrode arrangement, using a nickel cobalt manganese oxide electrode (NCM electrode, Toda Kogyo Europe GmbH) as working electrode and lithium foil (diameter 12 mm and 5 mm, respectively, Chemetall) as counterelectrode and reference electrode. In this example, a 1 M solution of lithium 1-trifluoromethoxy-1,2,2,2-tetrafluoroethanesulfonate prepared according to Example 1 in a mixture of 50% by weight of ethylene carbonate and 50% by weight of diethyl carbonate (EC:DEC, 1:1) was used.

FIG. 4 shows the discharge capacity or lithium deintercalation efficiency and the efficiency of the lithium-ion half-cell. The discharge capacity and efficiency are plotted against the number of cycles. As FIG. 4 shows, the half-cell with 1 M lithium 1-trifluoromethoxy-1,2,2,2-tetrafluoroethanesulfonate had a starting capacity of about 138 mAh g$^{-1}$ after the successful current rate stress test (C rate test) of the cell (I). After the subsequent cycling (II), the capacity in the 80th cycle was still about 137 mAh g$^{-1}$. In addition, the efficiency of the cell after 2 standard cycles rose to more than 99.6% of a maximum efficiency of 100%. It was found that the cell exhibited excellent cycling stability with the NCM cathode too.

Example 6

Cyclic Voltammetry

The cyclic voltammetry of a 1 M solution of lithium 1-trifluoromethoxy-1,2,2,2-tetrafluoroethanesulfonate prepared according to example 1 was conducted in a mixture of 50% by weight of ethylene carbonate and 50% by weight of diethyl carbonate (EC:DEC, 1:1).

The experiments were conducted in a 3-electrode arrangement in modified Swagelok® T-pieces (tube connector, stainless steel body) with a graphite electrode (Timcal T44 graphite material) as working electrode and lithium foil (diameter 12 mm and 4 mm, respectively, Chemetall) as counterelectrode and reference electrode. In addition, the cell body was lined with a polyester film siliconized on one side (Mylar®, PPI-SP 914, 100 μm) and the electrodes were introduced into the cell body. The electrodes were separated by a nonwoven fabric (Freudenberg®, FS2226E, 6 plies) which had been impregnated with the corresponding electrolyte.

FIG. 5 shows the results of the cyclic voltammetry for three cycles (1), (2) and (3). In FIG. 5, the intercalation and deintercalation phases identifiable by the increased current densities in the particular cycles are recognizable in the range between 0 and 0.3 V. This demonstrates the reversibility of the system.

The enlarged section of the range from 0.5 V to 1 V shows the formation of the solid electrolyte interphase (SEI) of the lithium 1-trifluoromethoxy-1,2,2,2-tetrafluoroethanesulfonate-carbonate electrolyte. In comparison is shown, the formation potential of the SEI for a 1 M solution of $LiPF_6$ in a mixture of 30% by weight of ethylene carbonate and 70% by weight of diethyl carbonate (EC:DEC, 3:7).

Example 7

Thermal Stability

The breakdown products of a 1 M solution of lithium 1-trifluoromethoxy-1,2,2,2-tetrafluoroethanesulfonate prepared according to example 1 in a mixture of 50% by weight of ethylene carbonate and 50% by weight of diethyl carbonate (EC:DEC, 1:1) were determined in comparison with the breakdown products of a 1 M solution of $LiPF_6$ (Sigma-Aldrich, battery grade) in a mixture of 30% by weight of ethylene carbonate and 70% by weight of diethyl carbonate (EC:DEC, 3:7).

The electrolytes were stored in a climate-controlled chamber at 95° C. for two weeks and subsequently analyzed by means of gas chromatography-mass spectrometry (Clarus GC 600 from Perkin Elmer).

FIG. 6 shows the breakdown products of the thermal aging at 95° C. of a 1 M solution of lithium 1-trifluoromethoxy-1,2,2,2-tetrafluoroethanesulfonate (LiB-8) in ethylene carbonate and diethyl carbonate (EC:DEC) in a ratio of 1:1 compared to 1 M $LiPF_6$ in EC:DEC in a ratio of 3:7. As FIG. 6 shows, for the 1 M lithium 1-trifluoromethoxy-1,2,2,2-tetrafluoroethanesulfonate electrolyte in EC:DEC, no carbonate breakdown products were found by means of GC-MS in the thermally aged electrolyte. In contrast, for the 1 M $LiPF_6$ electrolyte in EC:DEC, carbonate breakdown products were detected on the basis of the signals between 2.5 min and 3.5 min. The signal after 12 min is attributable to diethyl carbonate. This shows that the thermal stability of 1 M lithium 1-trifluoromethoxy-1,2,2,2-tetrafluoroethanesulfonate exceeded the stability of the $LiPF_6$ electrolyte.

These results show overall that lithium 1-trifluoromethoxy-1,2,2,2-tetrafluoroethanesulfonate is one possible substitute for $LiPF_6$ as conductive salt in lithium-ion batteries.

The invention claimed is:

1. A lithium-based energy storage means containing an electrolyte comprising lithium 1-trifluoromethoxy-1,2,2,2-tetrafluoroethanesulfonate, an organic solvent and an ionic liquid and/or a polymer matrix.

2. A lithium-based energy storage means containing an electrolyte comprising lithium 1-trifluoromethoxy-1,2,2,2-tetrafluoroethanesulfonate, an organic solvent and an additional ingredient selected from the group consisting of an ionic liquid, a polymer matrix and a combination of an ionic liquid and a polymer matrix.

3. A lithium-based energy storage means containing an electrolyte comprising lithium 1-trifluoromethoxy-1,2,2,2-tetrafluoroethanesulfonate and an ionic liquid.

4. A lithium-based energy storage means containing an electrolyte comprising lithium 1-trifluoromethoxy-1,2,2,2-tetrafluoroethanesulfonate and a polymer matrix.

5. The lithium-based energy storage means of claim 3, wherein the ionic liquid comprises 1-trifluoro-methoxy-1,2,2,2-tetrafluoroethanesulfonate and an organic cation.

6. The ionic liquid as claimed in claim 3, wherein the cation is selected from the group consisting of alkylammonium, pyridinium, pyrazolium, pyrrolium, pyrrolinium, piperidinium, pyrrolidinium, imidazolium and sulfonium compounds.

7. The ionic liquid as claimed in claim 3, wherein the cation is selected from the group consisting of N-butyl-N-methylpyrrolidinium, N-methyl-N-propyl-pyrrolidinium, 1-ethyl-3-methylimidazolium, 1-ethyl-2,3-dimethylimidazolium and 1-butyl-3-methyl-imidazolium.

* * * * *